Figure 1:
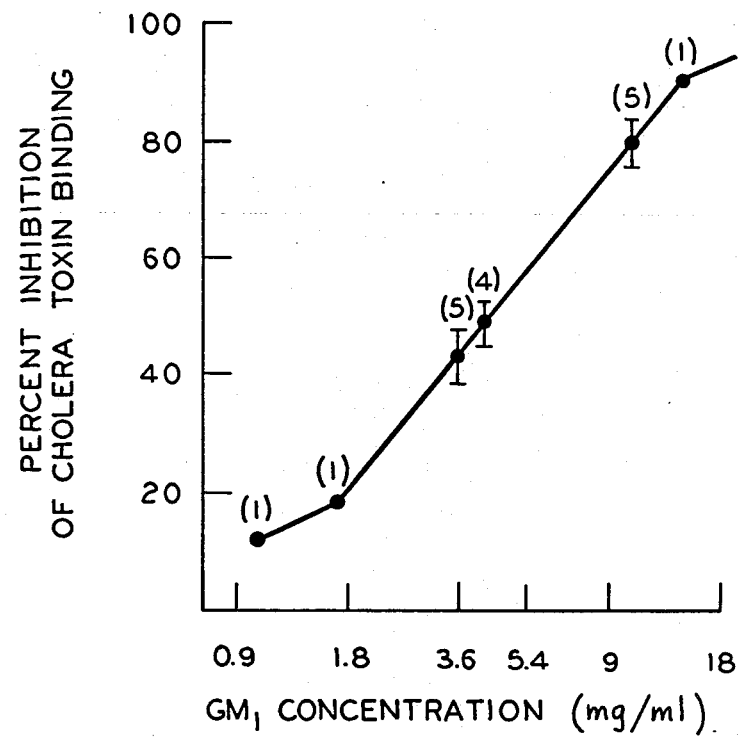

United States Patent [19]

Ginns et al.

[11] Patent Number: 4,469,795
[45] Date of Patent: Sep. 4, 1984

[54] RADIOASSAY FOR MONOSIALOGLYCOSPHINGOLIPID ($G_{M1}$) GANGLIOSIDE CONCENTRATION

[76] Inventors: Edward Ginns, 8617 Rayburn Rd., Bethesda, Md. 20817; Joseph French, 2 Belmont Pl., Staten Island, N.Y. 10301

[21] Appl. No.: 296,467

[22] Filed: Aug. 26, 1981

[51] Int. Cl.$^3$ .................... G01N 33/50; G01N 33/60
[52] U.S. Cl. .................................. 436/504; 424/1.1; 436/63; 436/71
[58] Field of Search .......................... 424/1, 1.5, 1.1; 436/501, 503, 504

[56] References Cited

U.S. PATENT DOCUMENTS 4,125,492 11/1978 Cuatrecasas et al. .................. 260/9
4,225,487 9/1980 Cuatrecasas et al. ................ 260/121

OTHER PUBLICATIONS

*Pediatric Research*, vol. 14(11) pp. 1276–1279(1980) Ginns et al.
*Proc. Society Experimental Biology & Medicine*, vol. 145(4), pp. 1187–1191, (1974) Peterson et al.
*J. Neurochemistry*, vol. 35(4), pp. 977–982 (1980), Ginns, E. and French, J.

*Primary Examiner*—Teddy S. Gron
*Assistant Examiner*—M. Moskowitz
*Attorney, Agent, or Firm*—Laff, Whitesel, Conte & Saret

[57] ABSTRACT

A radioassay test for the rapid and sensitive determination of the concentration of monosialoglycosphingolipid $G_{M1}$ ganglioside concentrations in small volumes of cerebrospinal fluid from individual patients is based on the high affinity interaction between cholera enterotoxin and $G_{M1}$ ganglioside. The level of $G_{M1}$ ganglioside present in the cerebrospinal fluid has been shown to be an indicator of active central nervous system pathology. In the present invention, the use of highly specific toxins eliminates cross reactivity with the other gangliosides, thereby eliminating the need to process the cerebrospinal sample prior to assay, except for centrifugation. Results of a specific application of the subject radioassay to newborn infants and older infants and children (some of the latter having active neurologic disease) indicated that the $G_{M1}$ ganglioside concentration in the cerebrospinal fluid is probably a function of both central nervous system tissue ganglioside content and turnover.

8 Claims, 3 Drawing Figures

RADIOASSAY FOR MONOSIALOGLYCOSPHINGOLIPID ($G_{M1}$) GANGLIOSIDE CONCENTRATION

This invention relates to a radioassay method of determining the concentration level of monosialoglycosphingolipid $G_{M1}$ ganglioside in the cerebrospinal fluid of patients, which may provide a valuable indication of central nervous system damage or disorders. More particularly, the present invention provides a radioassay technique for the above purpose which utilizes the high affinity interaction between cholera enterotoxin and $G_{M1}$ ganglioside in a unique measurement process.

Medical scientists have for some time theorized that neurological diseases in humans and other mammalian animals may result in the alteration of central nervous system $G_{M1}$ ganglioside concentration, pattern, and content. As a result, several techniques have been developed over the past several years to measure the ganglioside concentration. These have included electrophoretic processes; thin-layer, gas-liquid, and high performance liquid chromatography systems; absorbance and fluorescence spectrophotometry processes; immunoprecipitation systems; and enzyme-linked immumosorbent assay techniques. Also, electron microscopic and immunohistologic studies have also been conducted, utilizing the binding characteristics of specific gangliosides to specific antisera or toxins. These described processes and systems have limited usefulness in that they require large specimen volumes, and often necessitate the use of pooled samples. Further, these prior techniques do not yield results quickly and are relatively insensitive.

Additional techniques for developing clinical correlations and assay methods involving the presence of $G_{M1}$ ganglioside have been previously used. One such system includes the use of thin layer chromatography, which requires large amounts of pooled cerebrospinal fluid specimens to obtain measurable results. Another known system utilizes high-performance thin-layer chromatography and densitometric determination of brain gangliosides, while another uses an immunoassay based on plastic-absorbed gangliosides. These latter methods are also more time consuming than the present invention, and usually require a larger quantity of fluid on which to perform the assay.

Prior ganglioside assay methodologies that include derivatization, extraction, separation and lengthy incubation procedures have a minimum detection limit of ganglioside at least ten times higher than that of the present radioassay. The present radioassay requires a normal cerebrospinal fluid volume of only twenty to fifty microliters.

Therefore, the present invention has a primary objective the provision of a radioassay for the detection and measurement of $G_{M1}$ ganglioside concentration. A more particular object is to provide an assay of the type described which permits the timely determination of cerebrospinal fluid $G_{M1}$ ganglioside concentration in individual patients.

Yet another object of the present invention is the development of a rapid, sensitive radioassay for determining $G_{M1}$ ganglioside concentration in the cerebrospinal fluid using the high affinity binding of $G_{M1}$ ganglioside to cholera toxin or B subunit thereof as a means of producing a measurable quantum.

Another object of the present invention is to provide a unique and novel radioassay for determining $G_{M1}$ ganglioside concentration in cerebrospinal fluid which is fast, can be performed on relatively small sample volumes, and involves the use of highly specific toxins to eliminate cross reactivity with other components of the cerebrospinal fluid whereby the cerebrospinal fluid sample does not require processing prior to assay, except for centrifugation.

Yet another object of the present invention is to utilize the interaction between $G_{M1}$ ganglioside and cholera toxin or B subunit to determine unknown levels of $G_{M1}$ ganglioside after developing a standard curve.

Figure 2:
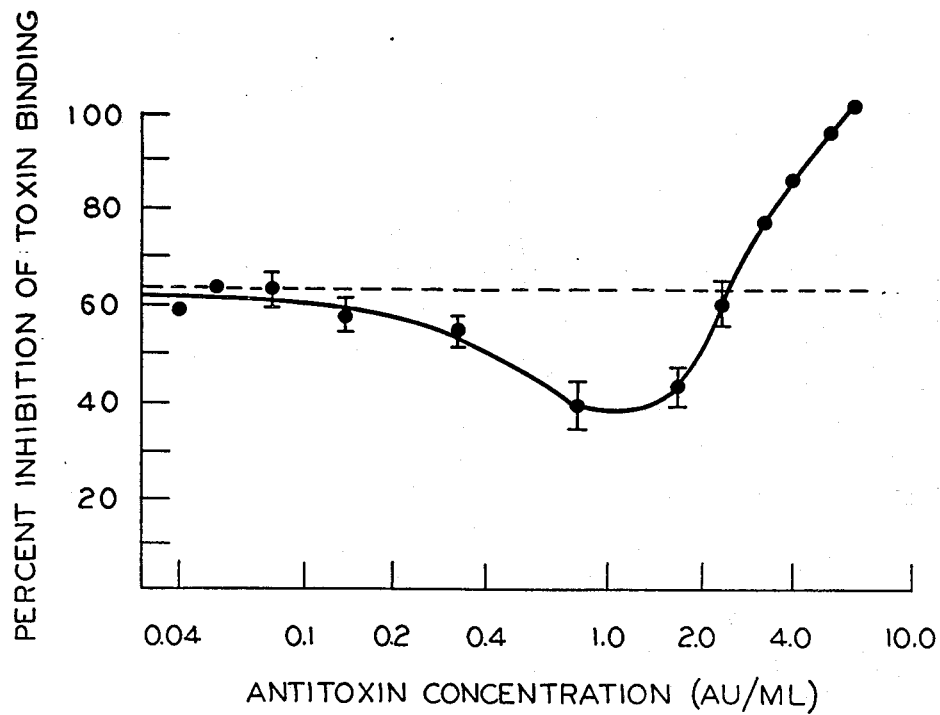
Figure 3:
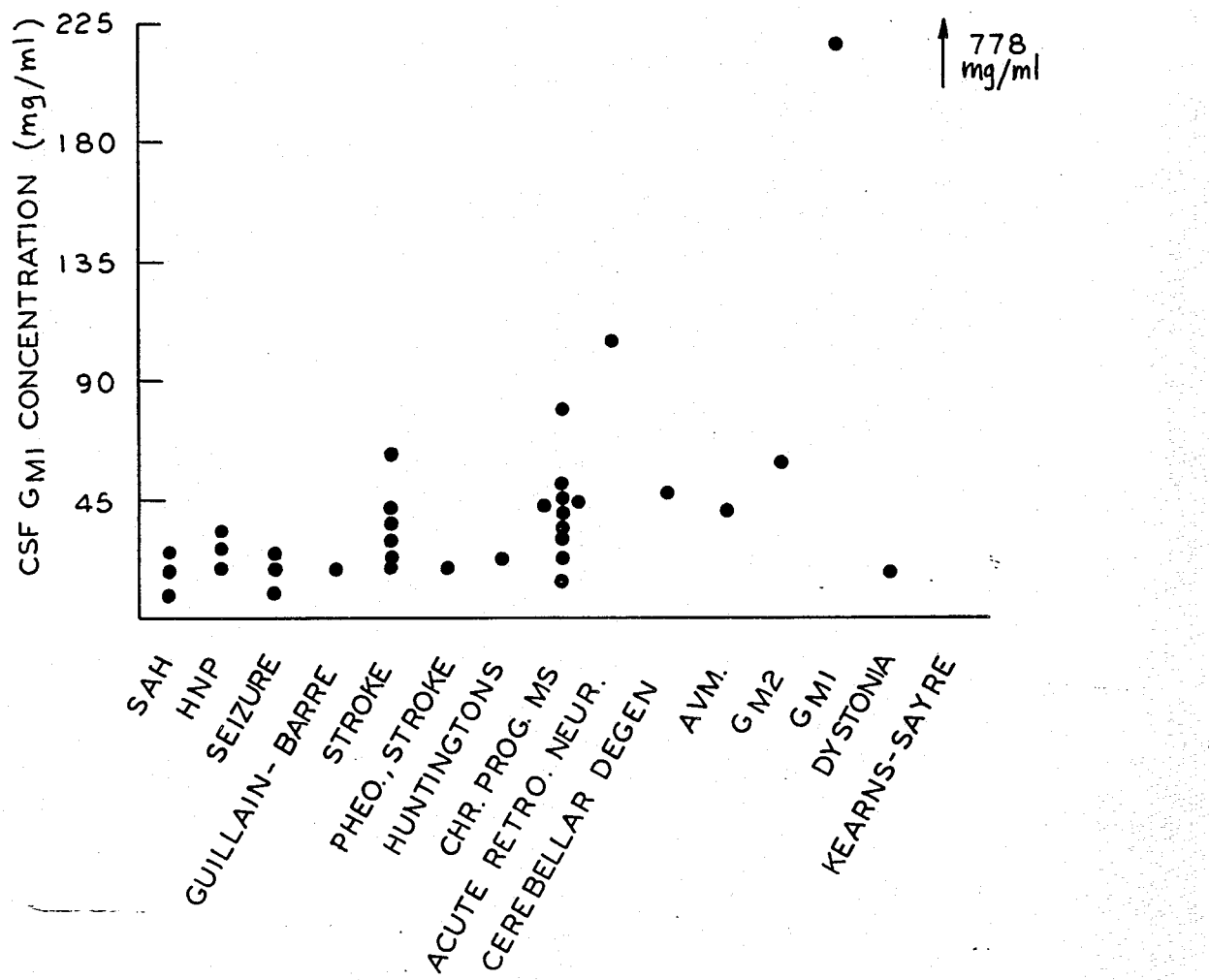

The above-mentioned and other features of this invention and the manner of obtaining them will become more apparent, and the invention itself will be best understood, by reference to the following description of an embodiment of the invention taken in conjunction with the accompanying drawings wherein:

FIG. 1 is a radioassay calibration curve showing the $G_{M1}$ ganglioside inhibition of cholera toxin binding to liver membranes, and FIG. 2 illustrates graphically the effect of purified cholera antitoxin on the measured $G_{M1}$ ganglioside inhibition of iodotoxin binding to liver membranes, and FIG. 3 is a graphic illustration of the degree of lumbar cerebrospinal fluid $G_{M1}$ ganglioside concentration in patients having specific neurological disorders.

The method associated with the preferred embodiment of the assay comprising our invention includes the steps of preparing a solution of $^{125}$Iodinated cholera toxin or B subunit, preparing an affinity binding matrix for cholera toxin such as a solution of concentrated liver membranes, preparing a solution containing $G_{M1}$ ganglioside, and performing a radioassay after adding measured amounts of $G_{M1}$ ganglioside, toxin and liver membrane as set forth in greater detail hereinbelow. From the data obtained from the radioassay, a standard calibration curve is prepared showing the degree of $G_{M1}$ ganglioside inhibition of cholera toxin binding to liver membranes. To obtain a diagnostic indication of neurological disorders in a particular patient, cerebrospinal fluid from the patient is obtained, the same radioassay procedure is followed, and the results are compared to the standard curve developed by the calibration assay. The difference in the degree of inhibition to binding of cholera toxin or B subunit to liver membranes will indicate the status of $G_{M1}$ gangliosides in the spinal fluid. As stated previously, the concentration of $G_{M1}$ gangliosides in the spinal fluid is a valuable indication of damage to or abnormalities in the central nervous system.

Regarding the perferred embodiment of the calibration assay itself, a solution of radioiodinated cholera toxin or B subunit is prepared for example by a modification of the Hunter and Greenwood procedure as described by Cuatrecasas (Interaction of Vibrio Cholerae Entertoxin With Cell Membranes, Biochem. 12, 3547-3558, 1973). In accordance with the substance of this procedure, one milligram of cholera toxin or 500 micrograms of cholera toxin subunit B is dissolved in 0.25 to 1.0 milliliter of buffer (50 mM Tris-HCl, 1 mM EDTA, 3 mM NaN$_3$ and 0.2 M NaCl, pH 7.5). This solution of buffered cholera toxin or subunit B is chromatographed on a ten to fifty milliliter (for example a 1.0×28 cm) Sephadex G75 (cholera toxin) or G50 (subunit B) column. This column preferably has been previously equilibrated with 100-250 millimolar sodium phosphate buffer pH 7.3 to 7.5. The same buffer is used to elute the cholera toxin. Iodination of the cholera toxin without prior chromatographic purification can be predicted to result in poor yields of iodinated toxin or subunit B.

An amount in the range of 10–100 micrograms of protein (either cholera toxin or subunit B) in buffer solution (100–200 microliters of 100–250 millimolar sodium phosphate buffer pH 7.4) and 0.5–5 millicuries of sodium $^{125}$iodide are next combined. Next, 20–50 micrograms of chloramine T are added. After 30–120 seconds, the reaction is terminated by the addition of 50–100 micrograms of sodium metabisulfite. Finally, 100–500 microliters of 0.1 molar sodium phosphate buffer, pH 7.4, with 0.1–1% bovine serum albumin are added to the reaction solution. This iodination reaction solution is applied to a 10–50 ml volume Sephadex G50 column that had been previously equilibrated with 0.1 M sodium phosphate buffer, pH 7.4, with 0.1–1% bovine serum albumin. The iodinated toxin or subunit B is eluted in the void volume fractions.

The iodinated toxin prepared as indicated in the paragraphs above is diluted (0.1 M sodium phosphate buffer, pH 7.4, 1% (w/v) BSA) to a protein concentration of approximately 200 ng/ml (500,000 cpm/50μ) for radioassay use. The iodinated cholera toxin is suitable for use in the radioassay even after storage for three months at −20° C.

Next, liver membranes, an affinity binding matrix for cholera toxin, are prepared from a 1:4 (w/v) 0.25 M sucrose homogenate as described by Cuatrecases (Affinity Chromatography and Purificaion of the Insulin Receptor of Liver Cell Membranes, Proc. Natl. Acad. Sci., U.S.A. 69, 1277–1281, 1972), except for the substitution of 0.1 M sodium phosphate buffer (ph. 7.4) for Tris-HCl buffer. It was found that Tris-HCl buffer eventually resulted in membrane preparations that inconsistently bound to $^{125}$Iodinated cholera toxin during the assay procedure, to be described. The following procedure is preferrable in preparation of the liver membranes, in accordance with the above-described reference. The hepatic tissue from ten adult rats are deemed sufficient to yield material for convenient preparative volumes. The homogenate is centrifuged for ten minutes at 600×g and decanted. The supernatant is recentrifuged for 30 minutes at 12000×g and decanted. Sufficient NaCl and $MgSO_4$ are added to the supernatant to yield 100 millimolar NaCl and 200 micromolar $MgSO_4$, and the solution is centrifuged for forty minutes at 40000×g and decanted. The pellet is suspended in 100–200 ml of 100 millimolar sodium phosphate buffer, pH 7.4, centrifuged for forty minutes at 40000×g, and decanted. The resedimented pellet is suspended again in buffer and recentrifuged for 40 minutes at 40000×g three additional times. The final pellet is suspended in 100 millimolar sodium phosphate buffer, pH 7.4 at a protein concentration of approximately 15 mg/ml, and stored at −20° C. in 500 microliter aliquots. Prior to use, the concentrated liver membranes are diluted to a concentration of 1.5 mg/ml with 100 millimolar sodium phosphate buffer, pH 7.4, with 1% bovine serum albumin.

Concentrated liver membrane preparations were found to be useable in the radioassay even after storage at −20° C. in 500 microliter aliquots for at least one year. Prior to use in the radioassay, the liver membranes are diluted to a protein concentration of 1.5 mg/ml with 0.1 M sodium phosphate buffer (ph. 7.4) that contained 1% (w/v) BSA. Diluted liver membranes were found to be useable for 1–2 weeks when stored at −20° C.

Protein concentrations of the liver membranes were determined by the method described by Lowry et al. (Lowry, O. H.; Rosebrough, N. J.; Farr, A. L.; and Randall, F. J.: "Protein Measurement with the Folin Reagent," Jour. Biol. Chem. 193, 265–275 (1951)). The liver membranes are next heated to 100° C. in 0.1 NaOH prior to protein determination. Crystalline BSA is used as the standard.

The next step in the assay process is the preparation of a standard solution of $G_{M1}$ ganglioside. This substance can be purchased from a supply source, or prepared by neuraminidase treatment of mixed bovine brain gangliosides, followed by Folch extraction, dialysis, and lyophilization.

In accordance with the latter procedure, 500–1000 milligrams of commercial bovine brain gangliosides are dissolved in 20–30 milliliters of 100–200 millimolar sodium acetate buffer, pH 5. One third of a unit of the enzyme neuraminidase is added and the rection solution incubated at 37° C. for 36 hours. At 12 and 24 hours, additions of one third units of neuraminidase to the reaction solution are made. At approximately 72 hours, the reaction is stopped by washing the solution with 5 volumes of 2:1 chloroform-methanol. The solution physicially separates. The upper phase contains the ganglioside. The lower phase is washed with theoretical upper phase (same liquid as upper phase, but without ganglioside) and the two upper phases are then combined. The methanol-containing upper phases are heated at 40°–50° C. under vacuum to remove the methanol. The remaining solution that contains the ganglioside $G_{m1}$ is dialyzed against distilled water for at least 24 hours. The final solution containing the $G_{M1}$ ganglioside can then be lypholyzed and stored at −20° C.

The weight percentage composition of an aliquot of a standard $G_{M1}$ ganglioside preparation is determined by densitometric evaluation of the resorcinal stained ganglioside pattern following thin-layer chromatography. Sialic acid content is determined by the thiobarbituric acid or resorcinol procedure. Both the weight percentage composition and total sialic acid content of the $G_{M1}$ ganglioside preparation are used to calculate the actual $G_{M1}$ ganglioside concentration of standard solutions. Standard solutions of $G_{M1}$ ganglioside are prepared in 0.1 M sodium phosphate buffer (pH 7.4 containing 1% (w/v) BSA) at a final concentration of 51 ng/ml and stored at −20° C. in 500 μl aliquots.

Following the preparation of the above materials, the radioassay of $G_{M1}$ ganglioside is preferrably performed in 12×75 MM plastic tubes at a constant volume.

Ganglioside, serum and CSF are agents which prevent binding of cholera toxin or B subunit to liver membranes. Cholera antitoxin can prevent or increase the binding of cholera toxin to liver membranes when the reaction is carried out in the presence of $G_{M1}$ ganglioside.

After the addition of a binding inhibiting agent which is either ganglioside, serum, cholera antitoxin, and/or CSF to the above preparation, the volume is adjusted to 100–200 μl with freshly prepared 0.1 M sodium phosphate buffer (pH 7.4) containing 1% (w/v) BSA. Following volume adjustment, 50 μl of $^{125}$iodinated cholera toxin or subunit B (approximately 10 ng/50 μl; 500,000 cpm/50 μl) in 0.1 M sodium phosphate buffer (pH 7.4) with 1% (w/v) BSA is added to the assay tubes. The assay solution is next mixed for 2–3 seconds and incubated for a total of 40-60 minutes (after introduction of the iodotoxin). Fifty microliters of liver membrane suspension (protein concentration approximately equal to 1.5 mg/ml; 0.1 M sodium phosphate buffer, pH 7.4 with 1% (w/v) BSA) is added and incubation at 4°-23° C. is continued for 10-20 minutes with intermittent shaking of the mixture. Incubation is terminated by the addition of 1-2 ml of deionized-distilled water.

The diluted mixture is filtered through a membrane, preferably a Millipore 25 mm EGWP Cellotate membrane that is supported by a multiple sample holder. The sample wells are washed two times with 5-10 milliliters of deionized-distilled water and the membranes then are transferred to disposable glass tubes for counting (1 minute) in a gamma counter. Incubation solutions without liver membranes provide corrections for non-specific binding of iodinated toxin to the Millipore filters.

CSF specimens are collected in glass or plastic tubes and stored at −60° C. or −20° C. until the time of assay. All specimens are assayed with fewer than three thawings. Specimens are thawed, mixed, and centrifuged to remove particulates (2000×g, 5 minutes) immediately prior to assay.

The results of the radioassay calibration are next depicted graphically, as shown in the typical radioassay calibration curve shown in FIG. 1. The curve shows that the inhibition of iodotoxin binding to liver membranes is a linear function of the $\log_{10}$ of the incubation solution $G_{M1}$ ganglioside concentration in the interval of approximately 2.5-12 ng/ml. The calibration curve does not significantly change over ten days.

In the preferred embodiment, approximately 50% of the radioactivity bound to liver membranes. The iodinated material that did not bind to liver membranes did not interfere with the ultimate radioassay measurement of $G_{M1}$ ganglioside concentration.

The non-specific binding of iodotoxin to the preferred Millipore filters was less than six percent of the total counts in the incubation solution. The binding of iodotoxin (10 ng/tube) at 23° C. to excess liver membranes (75 μl/tube) or $G_{M1}$ ganglioside (2 ng/tube) is complete in five and thirty minutes, respectively. There were no significant differences in the measured $G_{M1}$ ganglioside inhibition of iodotoxin binding to liver membranes when the BSA concentration in the $G_{M1}$ ganglioside solution aliquot was varied from 0 to 2 percent (w/v).

Radioassay determined total $G_{M1}$ ganglioside concentration in incubation solutions containing additions of standard $G_{M1}$ ganglioside solution and previously measured CSF was 107±2% (X±SD) of expected $G_{M1}$ ganglioside concentration. Preincubation of excess, unlabelled, purified cholera toxin (58 ng/tube) with either $G_{M1}$ ganglioside standard, CSF, or serum resulted in a greater than 92% reversal of inhibition of iodotoxin binding to liver membranes, when the iodotoxin was susequently added as specified in the routine assay. In the above-described procedure, inhibition of iodotoxin binding to liver membranes by the unlabelled entertoxin did not occur. Incubation of iodotoxin with excess $G_{M1}$ ganglioside was associated with a greater than 94% inhibition of liver membrane toxin binding.

FIG. 2 illustrates the effects of purified cholera antitoxin on the measured $G_{M1}$ ganglioside inhibition of iodotoxin binding to liver membranes. Incubation mixture antitoxin concentrations of less than 0.1 AU/ml did not significantly affect the inhibition of iodotoxin binding to liver membranes by $G_{M1}$ ganglioside. At antitoxin concentrations of between 0.1-3.0 AU/ml, the binding of iodotoxin was enhanced, and at higher antitoxin concentrations the binding was inhibited.

The following data was determined from applications of the above-described radioassay on various groups of patients. Serum from five normal adults resulted in inhibition of iodotoxin binding equivalent to a $G_{M1}$ ganglioside concentration of 27.8±2.7 ng/ml (X±SD); eight normal neonates had a mean serum equivalent $G_{M1}$ ganglioside concentration of 31.1±5.2 ng/ml (X±SD). The lumbar CSF $G_{M1}$ ganglioside concentrations in a small group of adolescent and adult patients with diverse neurological disorders is shown in FIG. 3. The $G_{M1}$ ganglioside concentrations (at birth) in the lumbar CSF of a normal and two low APGAR neonates were 52.1 ng/ml, 64.0 ng/ml, and 78.6 ng/ml, respectively. The repeat lumbar CSF $G_{M1}$ ganglioside concentrations at five days of age of the same three neonates were 51.2 ng/ml, 111.3 ng/ml and 154.6 ng/ml respectively. The lumbar CSF $G_{M1}$ ganglioside concentration and serum equivalent $G_{M1}$ ganglioside concentration of an adult patient with $G_{M2}$ gangliosidosis were 62.7±3.8 ng/ml and 43.3±2.6 ng/ml (X±SD), respectively. The lumbar CSF $G_{M1}$ ganglioside concentration of an adult patient with $G_{M1}$ gangliosidosis was 213±20 ng/ml (X±SD). The CSF $G_{M1}$ ganglioside concentration and serum equivalent $G_{M1}$ ganglioside concentration in a 12 year old with both shunted hydrocephalus and severe, chronic renal failure were 424 ng/ml and 29 ng/ml, respectively.

No correlation was found between CSF $G_{M1}$ ganglioside concentration and CSF erythrocyte, leukocyte, total calcium, glucose or total protein or serum bilirubin contents. The addition of buffer washed (0.1 M sodium phosphate, pH 7.4) adult human erythrocytes and leukocytes to CSF (hematocrit of approximately 6.4%) reduced measured $G_{M1}$ ganglioside concentration by 7.9%. Prior storage, −20° C., of this sanguinous CSF yielded only a 4.8% decrease of measured $G_{M1}$ ganglioside concentration. The addition of serum to CSF (radioassay incubation solution total protein of 800 mg%) reduced radioassay measured $G_{M1}$ ganglioside concentration by only 13%.

The reported data from recovery, excess $G_{M1}$ ganglioside incubation, and preincubation with unlabelled cholera toxin, support the conclusion that the sensitivity of this radioassay for lumbar CSF $G_{M1}$ ganglioside concentration is a function of both the specific activity of $^{125}$iodinated cholera toxin and the concentration of the iodotoxin in the incubation solution. Thus, the described radioassay technique permits a valid measurement of total $G_{M1}$ ganglioside concentration in CSF.

The radioassay measurement of serum inhibition of iodotoxin binding to liver membranes is expressed as equivalent $G_{M1}$ ganglioside concentration since both glycoproteins and cholera antitoxin antibodies can result in interference with the determination of $G_{M1}$ ganglioside concentration in serum. The equivalent $G_{M1}$ ganglioside concentration of serum represents the maximum contribution by serum contamination to the radioassay determined CSF $G_{M1}$ ganglioside concentration.

Cholera antitoxin intereference with the radioassay measurement of $G_{M1}$ ganglioside concentration is not significant for assay incubation solutions containing less than 0.12 antitoxin units/ml (FIG. 2). A recent study of anti-cholera toxin titers in subjects living in a non-endemic region in the northeast United States indicates that all studied sera have antitoxin titers less than 3 AU/ml (Blake, P., Allegra, D., Snyder, J., Barrett, T., McFarland, L., Caraway, C., Feeley, J., Craig, J., Lee, J., Puhr, H., and Feldman, R., (1980) Cholera—A Possible Endemic Focus In The United States, N.Eng.J.Medicine: 302, 305-309). Thus, even if the blood-brain barrier is disrupted, fifty microliter aliquots of CSF specimens containing less than 1000 mg% total protein (with corresponding serum antitoxin titers of less than 3 AU/ml) have neither antitoxin titers nor glycoprotein levels that will significantly interfere with the measurement of $G_{M1}$ ganglioside concentration by the present radioassay procedure. Therefore, in patients that have a CSF total protein concentration of less than 1000 mg% and a serum antitoxin titer of less than 3 AU/ml, the reported methodology permits a valid assessment of CSF $G_{M1}$ ganglioside concentration.

The above-described radioassay has been applied to the longitudinal measurement of lumbar CSF $G_{M1}$ ganglioside concentration in neonates and children. The temporal evolution and the magnitude above baseline values of lumbar CSF $G_{M1}$ ganglioside concentration is considered to be effective in reflecting brain tissue damage, and may be a severity predictor of neonatal central nervous sytem injury. Also, correlation of preliminary data with the clinical status of a small group of newborn infants suggests that the temporal pattern of cerebrospinal fluid $G_{M1}$ ganglioside concentration during a period of injury may be a sensitive indicator of the severity of acquired central nervous system damage.

In conducting the radioassay on neonates and children, cerebrospinal fluid samples are collected in tubes, such as glass or plastic and stored at $-20°$ C. or $-60°$ C. until the time of assay. Prior to assay, samples are thawed, mixed, and centrifuged ($2000 \times g$, 5 minutes) to remove particulates.

The radioassay for $G_{M1}$ ganglioside has been described above. First, a calibration curve is prepared. Briefly, after addition of 20-50 $\mu$l of an appropriate dilution of ganglioside standard or CSF to $12 \times 75$ mm plastic tubes, the volume is adjusted to 150 $\mu$l with freshly prepared 0.1 M sodium phosphate buffer (pH 7.4) containing 1% (w/v) bovine serum albumin. Fifty microliters of $^{125}$iodinated cholera toxin (approximately 10 ng/50 $\mu$l; 500,000 cpm50 $\mu$l) is added to the assay tube, the solution mixed for 2-3 seconds, and incubated for a total of forty minutes (after the addition of iodotoxin). Fifty microliters of liver membrane suspension (protein concentration of 1.5 mg/ml) is added and incubation at 23° C. is continued for 10 minutes with intermittent shaking of the mixture. Incubation is terminated by the addition of 2 ml of distilled-deionized water. The diluted mixture is filtered through a Millipore EGWP 25 mm Cellotate membrane, and the membrane subsequently transferred to a disposable glass or plastic tube for counting (1 minute) in a gamma counter. A typical standard curve as shown in FIG. 1 is next prepared.

Next, in the example forming the basis of this embodiment of the invention, single samples of cerebrospinal fluid were obtained from 17 neonates and 17 older pediatric patients ranging in age from 5 weeks to 18 years. Lumbar punctures had been performed for evaluation of suspected sepsis, fever associated seizures, or failure to thrive. Serial samples were available from three additional neonates.

In several neonates considered healthy babies but with diverse perinatal complications, the mean CSF $G_{M1}$ ganglioside concentration was $76.6 \pm 27.4$ ng/ml ($X \pm SD$; range 35.8-129.6 ng/ml). The range of initial lumbar CSF $G_{M1}$ ganglioside concentrations in three neonates in which subsequent lumbar punctures were performed was 53.1-80.1 ng/ml. In two of these cases, the measured CSF $G_{M1}$ ganglioside concentration subsequently increased and remained elevated above initial values. No serial increase in CSF $G_{M1}$ ganglioside concentration was noted in one of these cases, and in these three neonates, CSF myelin basic protein was detectable only in the terminal sample from one case (6.4 ng/ml).

The mean lumbar CSF $G_{M1}$ ganglioside concentration in 9 pediatric age patients without nervous sytem pathology and in 8 children with active neurologic disease were $31.9 \pm 22.2$ ng/ml ($X \pm SD$; range: 4.8-70.0 ng/ml) and $53.1 \pm 30.0$ ng/ml ($X \pm SD$; range: 6.1-94.5 ng/ml), respectively.

The addition of buffer washed (0.1 M sodium phosphate, pH 7.4) adult human erythrocytes and leukocytes to CSF (hematocrit of approximately 6.4%) reduced measured $G_{M1}$ ganglioside concentration by 7.9%. Prior storage, $-20°$ C., of this sanguinous CSF yielded only a 4.8% decrease of measured $G_{M1}$ ganglioside concentration. The addition of serum to CSF (radioassay incubation solution total protein of 800 mg/dl) reduced radioassay measured $G_{M1}$ ganglioside concentration by only 13%.

It is apparent that the study of cerebrospinal fluid $G_{M1}$ ganglioside concentration in newborn infants and children indicates the versatility of the $G_{M1}$ ganglioside radioassay. This radioassay permits the rapid measurement of $G_{M1}$ ganglioside concentration in small aliquots of cerebrospinal fluid from individual patients. Data from prior studies of adult patients with diverse neurological disorders has indicated that the increase in CSF $G_{M1}$ ganglioside concentration is not specific for a single disease process. Our lower range values of CSF $G_{M1}$ ganglioside concentration in children older than 28 days of age, who had fever associated seizures and/or suspected pyogenic leptomeningitis, agree with the lower range of radioassay CSF $G_{M1}$ ganglioside concentration found in adults.

The present study does not document a "true" normal CSF $G_{M1}$ ganglioside concentration at all ages. The lower range of pediatric and adult CSF $G_{M1}$ ganglioside radioassay concentration is similar to the previously reported normal adult CSF values. The specimens of CSF that we studied were obtained from patients with diverse toxic-neuropathological processes. We can thus conclude that certain disease states result in minimal, if any, elevation above normal values of single, isolated measurements of CSF $G_{M1}$ ganglioside concentration.

In our study, the mean cerebrospinal fluid $G_{M1}$ ganglioside concentration of neonatal subjects is greater than that of older infants and children. Prior available data indicates that the $G_{M1}$ ganglioside sialic acid concentration in the human infant brain is greater than that in human adult brain. However, the adult and newborn values of brain total ganglioside sialic acid content do not differ. Prior commentators also concluded that the lumbar CSF ganglioside pattern is similar to that of brain. Thus, from the data obtained from the present invention, we can conclude that the increase in radioassay determined CSF $G_{M1}$ ganglioside concentration in neonates and in patients with neuropathologic processes indicats that the CSF $G_{M1}$ ganglioside concentration is probably a function of both central nervous system tissue ganglioside content and turnover.

No prognostic significance was found of single CSF $G_{M1}$ ganglioside concentration determinations in individual newborn infants who were being evaluated for possible sepsis, seizures, or failure to thrive. However, the temporal evolution above baseline values of CSF $G_{M1}$ ganglioside concentration in three neonates did correlate with the clinical neuropathologic status of these patients.

Single assays of CSF myelin basic protein concentration in individual newborn infants and children may indicate severe brain tissue destruction. No prognostic significance was noted in our individual or serial measurements of CSF myelin basic protein in the three neonates whose temporal pattern of CSF $G_{M1}$ ganglioside concentration was studied. Cerebrospinal fluid myelin basic protein concentration is a less sensitive indicator of acute neonatal central nervous system injury than serial CSF $G_{M1}$ ganglioside concentrations. This may be accounted for by the relative paucity of central nervous system myelin in the human newborn.

The data reported in the above described test on neonates and children suggest that alterations of newborn central nervous sytem ganglioside concentration and/or turnover can be observed by determining the temporal evolution of neonatal CSF $G_{M1}$ ganglioside concentration. During the acute phase of injury, altered temporal patterns of CSF $G_{M1}$ ganglioside concentration may be a sensitive indicator of central nervous system damage.

Those skilled in the art will readily perceive changes and modifications which may be made in the disclosed invention. Therefore, the appended claims are to be construed broadly enough to cover all equivalent procedures and formulations falling within the scope and spirit of the invention.

We claim:

1. A method of conducting a radioassay for $G_{M1}$ ganglioside concentration in cerebrospinal fluid utilizing the high affinity interaction between cholera enterotoxin and $G_{M1}$ ganglioside comprising the steps of preparing a radioiodinated cholera toxin solution, preparing liver membranes from a 0.25 M sucrose homogenate, preparing several quantities of known $G_{M1}$ ganglioside concentration in solution, obtaining a count of 125 iodine cholera toxin bound to liver membranes by means of radioassay of various mixtures of said iodotoxin solution, liver membranes and respective $G_{M1}$ ganglioside solutions, preparing a standard curve showing the variation in inhibition of cholera toxin binding to liver membranes for different mixtures of $G_{M1}$ ganglioside concentrations, repeating the above steps on a solution of unknown $G_{M1}$ ganglioside concentrations and comparing the results of said repeated steps with said standard curve to determine the amount of said unknown $G_{M1}$ ganglioside concentration.

2. The method of claim 1 whereas said cholera enterotoxin is subunit B of cholera enterotoxin.

3. The method of claim 1 where said step of preparing a radioiodinated cholera toxin solution includes the sub-steps of:
   (a) dissolving one milligram of cholera toxin in 0.25-1.0 milliliters of buffer;
   (b) chromatographing said solution of buffered cholera toxin on a 10-50 milliliter column;
   (c) combining 10-100 micrograms of the foregoing solution with 0.5-5 millicuries of sodium $^{125}$iodide;
   (d) adding 20-50 micrograms of chloramine T to form a reaction solution;
   (e) terminating the reaction after 30-120 seconds by the addition of 50-100 micrograms of sodium metabisulfite;
   (f) adding 100-500 microliters of 0.1 molar sodium phosphate buffer and 0.1-1% bovine serum albumin to the reaction solution;
   (g) eluting the iodonated cholera toxin; and
   (h) diluting the iodonated cholera toxin.

4. The method of claim 3 wherein said cholera toxin is subunit B of said cholera toxin.

5. The method of claim 3 wherein step (a) is immediately followed by the additional step of:
   (b) equilibrating said column with 100-250 millimolar sodium phosphate buffer pH7.3-7.5.

6. The method of claim 1 wherein said step of preparing liver membranes from a 0.25 M sucrose homogenate includes the sub-steps of:
   (a) centrifuging and decanting said liver membranes to form a supernatant;
   (b) recentrifuging and decanting said supernatant;
   (c) adding sodium chloride and magnesium sulphate to said supernatant to yield 100 millimolar sodium chloride and 200 micromolar magnesium sulphate;
   (d) centrifuging and decanting said solution to form a pellet;
   (e) suspending said pellet in 100-200 ml of 100 millimolar sodium phosphate buffer, centrifuging and decanting same to form a resedimented pellet;
   (f) suspending said resedimenteed pellet in a buffer solution and recentrifuging three times to form a final pellet;
   (g) suspending said final pellet in a 100 millimolar sodium phosphate buffer at a protein concentration of approximately 15 mg/ml; and
   (h) diluting said final pellet to a concentration of 1.5 mg/ml with 100 millimolar sodium phosphate buffer with 1% bovine serum albumin.

7. The method of claim 1 wherein said step of preparing several quantities of known $G_{M1}$ ganglioside concentration includes the sub-steps of:
   (a) dissolving 500-1000 milligrams of bovine brain gangliosides in 20-30 milliliters of 100-200 millimolar sodium acetate buffer to form a solution;
   (b) adding one-third unit of neuraminidase enzyme and incubating the reaction solution at 37° C. for 36 hours;
   (c) adding one-third unit of neuraminidase enzyme to said reaction solution at 12 and 24 hours;
   (d) halting the reaction solution at approximately 72 hours by washing the solution with five volumes of 2:1 chloroform-methanol, thereby producing an upper phase and a lower phase, said upper phase containing said ganglioside;
   (e) washing said lower phase with a theoretical upper phase solution equivalent to said upper phase but free of said ganglioside, and combining said upper phases;
   (f) heating said methanol-containing upper phases at 40°-50° C. under vacuum to remove said methanol, and
   (g) dialyzing the remaining ganglioside-containing solution against distilled water for approximately 24 hours.

8. The method of claim 1 wherein the step of obtaining a 125 iodine count by means of radioassay of the mixture of radioiodinated toxin, liver membrane, and $G_{M1}$ ganglioside solution includes:
(a) adding $G_{M1}$ ganglioside to a suitable receiving tube;
(b) adjusting the volume of the solution to 100–200 μl by means of 0.1 M sodium phosphate buffer (pH 7.4) containing 1% (w/v) BSA;
(c) adding 50 μl of $^{125}$iodinated cholera toxin in 0.1 M sodium phosphate buffer (pH 7.4) with 1% (w/v) BSA;
(d) mixing the mixture for 2–3 seconds;
(e) incubating the mixture at 4–23° C. for 40–60 minutes;
(f) adding 50 μl of liver membrane suspension;
(g) continuing incubation of 4°–23° C. for 10–20 minutes with intermittent shaking of the mixture;
(h) adding 2 ml of deionized-distilled water;
(i) filtering the mixture;
(j) washing the mixture twice with 5–10 ml deionized-distilled water; and
(k) counting the radioactivity of the mixture with a gamma counter.

* * * * *